(12) United States Patent
Maida, Jr.

(10) Patent No.: US 6,933,491 B2
(45) Date of Patent: Aug. 23, 2005

(54) REMOTELY DEPLOYED OPTICAL FIBER CIRCULATOR

(75) Inventor: John L. Maida, Jr., Houston, TX (US)

(73) Assignee: Weatherford/Lamb, Inc., Houston, TX (US)

(*) Notice: Subject to any disclaimer, the term of this patent is extended or adjusted under 35 U.S.C. 154(b) by 278 days.

(21) Appl. No.: 10/317,703

(22) Filed: Dec. 12, 2002

(65) Prior Publication Data

US 2004/0113104 A1 Jun. 17, 2004

(51) Int. Cl.[7] ................................................ H01J 5/16
(52) U.S. Cl. ............................ 250/227.14; 250/227.18; 385/41
(58) Field of Search ........................ 250/227.14–227.18, 250/227.24, 573–574; 385/39, 41, 42; 356/317, 320; 600/317

(56) References Cited

U.S. PATENT DOCUMENTS

| | | | |
|---|---|---|---|
| 5,329,811 A | 7/1994 | Schultz et al. ................. | 73/155 |
| 5,341,805 A | 8/1994 | Stavridi et al. | |
| 5,361,313 A | 11/1994 | O'Keefe ....................... | 385/11 |
| 5,569,911 A | 10/1996 | Tomlinson, Jr. et al. | |
| 5,570,437 A | 10/1996 | Kluth et al. ................... | 385/12 |
| 5,582,064 A | 12/1996 | Kluth ............................ | 73/4 R |
| 5,986,749 A | 11/1999 | Wu et al. ...................... | 356/73.1 |
| 5,999,313 A | 12/1999 | Fukushima ................... | 359/484 |
| 6,006,832 A | 12/1999 | Tubel et al. ................... | 166/250.021 |
| 6,088,491 A | 7/2000 | Sorin et al. ................... | 385/11 |
| 6,094,284 A | 7/2000 | Huber | |
| 6,111,695 A | 8/2000 | Lee et al. ..................... | 359/484 |
| 6,139,797 A | 10/2000 | Suzuki et al. | |
| RE37,283 E | 7/2001 | Kluth et al. ................... | 385/12 |
| 6,256,588 B1 | 7/2001 | Maida, Jr. et al. ............ | 702/14 |
| 6,285,806 B1 | 9/2001 | Kersey et al. | |
| 6,301,045 B1 | 10/2001 | Liu ............................... | 359/484 |
| 6,310,989 B1 | 10/2001 | Liu ............................... | 385/11 |
| 6,370,287 B1 | 4/2002 | Liu ............................... | 385/11 |
| 6,377,720 B1 | 4/2002 | Kokkelink ................... | 385/11 |

FOREIGN PATENT DOCUMENTS

EP     0 660 106     8/1994

OTHER PUBLICATIONS

Kersey, A.D. "A Review of Recent Developments in Fiber Optic Sensor Technology", *Optical Fiber Technology* 1996, vol. 2; 291–317.

Kragas, T.K.; Williams, B.A.; Myers, G.A., "The Optic Oil Field: Deployment and Application of Permanent In–Well Fiber Optic Sensing Systems for Production and Reservoir Monitoring", *SPE* 71529, 2001.

Ahn, J.T.; Jeon, M.–Y.; Kim, K.H., "Two–Stage Reflective–Type Erbium–Doped Fiber Amplifier with Enhanced Noise Figure Characteristics", *Optics Communications* 2001, vol. 197; 121–125.

Liaw, S.–K.; Chi, S., "Repeated Bidirectional Transmission Using Two 4–Port Optical Circulators and a Bidirectional EDFA Without Isolators", *Optical Fiber Technology* 1999, vol. 5; 253–259.

Fujii, Y., "Polarization–Independent Optical Circulator Having High Isolation Over A Wide Wavelength Range", *IEEE Photonics Technology Letters* 1992, vol. 4; 154–156.

U.K. Search Report, Application No. GB0328865.1, dated May 28, 2004.

*Primary Examiner*—Stephone B. Allen
(74) *Attorney, Agent, or Firm*—Moser, Patterson & Sheridan, L.L.P.

(57) ABSTRACT

Fiber-optic-based systems and methods for monitoring physical parameters using a remotely deployed circulator are disclosed. In a preferred embodiment the circulator is remotely deployed with respect to an optical source/detector and coupled thereto by two dedicated fiber optical cables: a forward line for passing light from the source through the circulator to fiber-optic-based sensors, and a return line for passing light reflected from the sensors through the circulator back to the detector. By using separate forward and return lines in conjunction with the circulator, backscattering phenomenon experienced on the forward line will not interfere with the reflected light signals coming from the sensors. The circulator, and hence the sensors, may therefore be remotely deployed from the source/detector present at a monitoring station, greatly expanding distances which optical sensing systems can span.

41 Claims, 9 Drawing Sheets

REMOTELY DEPLOYED OPTICAL FIBER CIRCULATOR

BACKGROUND OF THE INVENTION

1. Field of the Invention

The present invention relates generally to the field of optical fiber signal transmission. More particularly, it relates to apparatus and methods for the remote measurement of physical parameters using fiber optic elements including a remote optical circulator in a system of optical fiber cables and optical fiber sensors.

2. Description of Related Art

As oil and gas reserves have been increasingly consumed over the years, the extraction of these hydrocarbons has become more difficult. The resultant development and exploitation of remote oil and gas resources in increasingly difficult operating environments such as deep water have given rise to numerous new technological challenges. Notably, there is an increased need for reserves and wells to be more widely monitored, especially for those hydrocarbon reserves lying deep below the ocean seabed.

Recent developments in fiber optic sensing technology, such as optical fiber sensors and optical fiber cables to link the sensor to the measurement instrumentation, have resulted in new and improved alternatives to the conventional electronic systems used in downhole production and reservoir monitoring. Optical fiber technology offers numerous advantages over past electronic monitoring systems, as they are able to withstand high pressures and temperatures. Furthermore, optical fiber systems and optical fiber sensors are typically of a structure and diameter similar to the optical fiber cable itself, allowing for easy incorporation into the downhole system.

In-well fiber optic systems measure such parameters as temperature, pressure, flow rate, fluid phase fraction, and seismic response, among other things. In such systems, light is sent along a single optical pathway (e.g., an optical fiber), and is reflected from the optical sensors such a Bragg grating sensors coupled to or incorporated with the pathway. The reflected light, indicative of the measured parameters, is sent back along the optical pathway for analysis. Such optical systems combine a high level of reliability, accuracy, resolution, and stability, and permit the multiplexing of several sensors along the optical pathway, thus enabling complex and multilateral wells to be fully instrumented with a single optical array. Through the use of such advanced fiber optic systems, real-time downhole data can be retrieved and analyzed to greatly improve production management and reservoir recovery. The value of such real-time, downhole monitoring systems offer the promise of achieving high levels of performance with low costs.

However, the use of fiber optic systems in such environments has resulted in several significant problems that have limited their use to date. Optical scattering phenomenon, such as Rayleigh backscatter in reflective single-fiber optic sensor transmission line systems, can limit the achievable deployment distances. Similarly, Mie (scattering of visible light wavelengths by spherical particles), Brillouin (scattering due to the interaction of laser light with sound waves) and Raman (scattering of laser light as it passes through a transparent medium) scattering phenomena further limit the distance over which optical sensing systems can be employed due to the elevated signal-to-noise ratio they cause. Other optical scattering noise such as Freznel (reverse propagating) reflections due to the connectors or couplers used in optical fiber technology can further contribute to high signal-to-noise ratio. These intrinsic (Raman, Mie, Brillouin, Rayleigh) and extrinsic (Freznel) effects add to the limit of achievable deployment distances in optical fiber monitoring technology, and suggest that expensive lower-loss fiber optic splices, instead of connectors or couplers, should be used when connecting components together along the array.

While there have been numerous patents and publications describing methods for measuring physical parameters using fiber optic systems, few address the issue of backscatter noise and limited monitoring distance. See, e.g., U.S. Pat. No. 5,361,313 to O'Keefe (describing a fiber optic sensor capable of detecting multiple parameters in remote locations using a combination of polarized light and multi-mode fiber optics); U.S. Pat. No. 5,582,064 to Kluth (describing a remotely deployable pressure sensor with a pressure communicating means operable by remote control); U.S. Pat. No. 6,006,832 to Tubel (describing a method and system for monitoring a formation surrounding a borehole in which a remote central control center communicates information with remote well platforms via telephone or wirelessly via satellite). Other approaches to this problem involve amplification of the reflected signals at the wellhead. However, these approaches suffer from several limitations. First, electronic equipment may be unable to withstand the harsh conditions of a downhole system, and in the event of a failure or breakdown would be very difficult and expensive to retrieve. Similarly, while placing an amplifier at the wellhead would increase the amplitude of the reflected signal, the associated noise of optical backscattering phenomena would increase as well.

What is needed is an optical fiber monitoring system that will allow for the remote measurement of physical parameters over significant distances without being limited by optical scattering phenomena.

SUMMARY OF THE INVENTION

Fiber-optic-based systems and methods for monitoring physical parameters using a remotely deployed circulator are disclosed. In a preferred embodiment the circulator is remotely deployed with respect to an optical source/detector and coupled thereto by two dedicated fiber optical cables: a forward line for passing light from the source through the circulator to fiber-optic-based sensors, and a return line for passing light reflected from the sensors through the circulator back to the detector. By using separate forward and return lines in conjunction with the circulator, backwards-propagating optical scattering noise phenomenon experienced on the forward line will not interfere with the reflected light signals coming from the sensors. The circulator, and hence the sensors, may therefore be remotely deployed from the source/detector present at a monitoring station, greatly expanding distances which optical sensing systems can span. In one embodiment, the circulator is integrated with a wellhead that sits on top of the ocean floor, and allows the wellhead to be deployed at greater distances than were before achievable.

BRIEF DESCRIPTION OF THE DRAWINGS

The features of the present invention may best be understood by reference to the following description of the presently preferred embodiments, together with the accompanying drawings in which.

DESCRIPTION OF ILLUSTRATIVE EMBODIMENTS

The present invention relates to a system for monitoring and controlling production wells from a remote location using fiber optic technology. In particular, in an embodiment of the present invention, an optical circulator is remotely located within a wellhead at the top of the oil or gas well, and a separate return fiber is provided from the circulator back to the control system. In this manner, backwards-propagating optical scattering noise is minimized or eliminated, resulting in an improved optical signal-to-noise ratio and improved deployment distance of the fiber optic monitoring system.

Figure 1A:
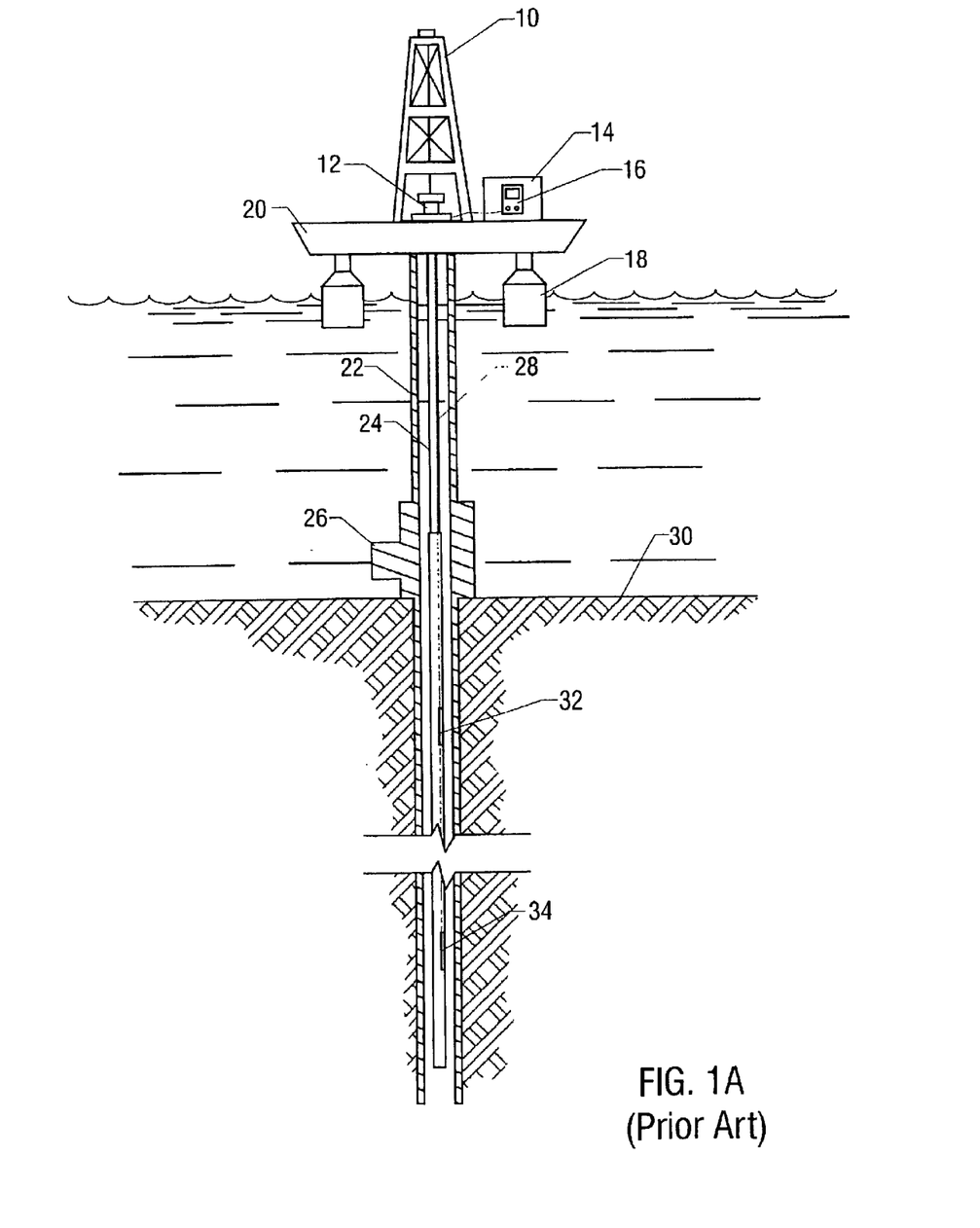
FIG. 1A illustrates a prior art system for a fiber optic monitoring system useful in monitoring the parameters within a well drill in the ocean floor.

A typical arrangement for an offshore fiber optic monitoring system according to the prior art is shown in FIG. 1A. Such an arrangement typically includes a floating workstation 18 or similar deep-water production system (e.g. fixed-leg platform, compliant tower, tension-leg platform (TLP), semi-submersible platform, or spar platform system) stationed over a submerged worksite on the ocean floor 30. The floating workstation 18 typically has a workdeck 20 supporting a derrick 10 with a hoisting means 12. The workstation 18 also has a control station 14, which contains a surface instrumentation unit 16. A fiber optic cable 28 runs from the instrumentation unit 16 along production tubing string 24 into wellhead 26. A casing 22 protects the fiber optic cable 28 and production tube from the harsh environment.

From wellhead 26, fiber optic cable 28 is run downhole, where a series of connectors or couplers 32 aid in providing light transmission to and from the downhole sensor assembly 34. These connectors or couplers 32, as well as the in-well fiber optic cable 28, are specifically designed for mechanical and environmental robustness, and typically incorporate multiple protective barriers between well bore fluids and the optical fiber. The sensor assembly 34 typically consists of optical fiber sensors and transducers, as well as the mandrel and other equipment required to integrate the assembly into the production tubing string. Many such fiber-optic-based sensors or sensor assemblies 34 are known, and can monitor a host of down hole parameters such as pressure, temperature, production flow rates, etc. For example, fiber Bragg grating (FBG) based sensors or sensor assemblies have proven useful in measuring such downhole parameters, and may be configured in interferometric arrangements, and/or time-division or wavelength-division multiplexed along a single optical fiber cable. However, using the system of FIG. 1A, and due to backscattering along the length of the optical fiber cable 28, the sensor 34 can be located at a maximum of about 9 kilometers from the surface instrumentation 16.

Figure 1B:
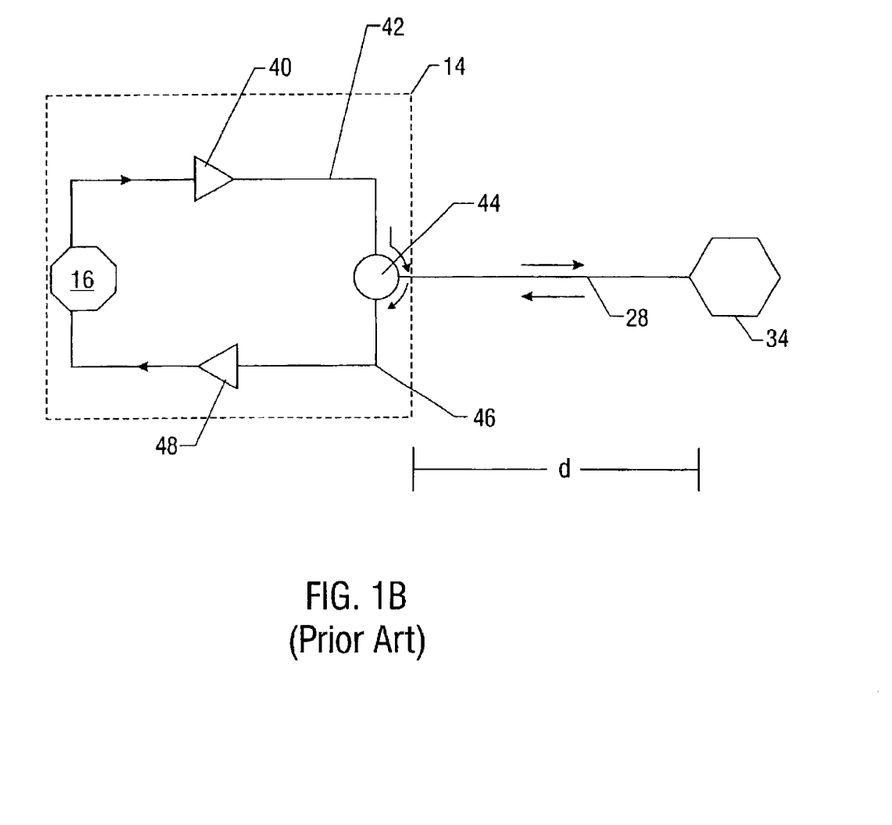
FIG. 1B illustrates a prior art system for transmission and analysis of light useful in the system of FIG. 1A.

Referring now to FIG. 1B, a schematic of how fiber optic systems such as those shown in FIG. 1A have previously been utilized is illustrated. Control station 14 houses the instrumentation unit 16, optical fibers 42 and 46, optical transmitter 40, optical receiver 48, and optical circulator 44. In standard implementations, the instrumentation is designed to reside in a control room environment and interface with an external data management system using protocols known in the art. Instrumentation unit 16 consists of a fiber optic light source (e.g. a laser), a light source detector, a signal demodulation unit, and a computer containing the software required to control the data acquisition, conversion, storage and interfacing. In a typical setting, a laser sends a light signal through optical transmitter 40 via outward propagating optic fiber 42, which is then directed through optical circulator 44. The signal travels outward over distance 'd' (again, typically no more than about 9 km) though a single bi-directional optic fiber 28 to sensor assembly 34, again, which preferably (but not necessarily) travels through the wellhead 26. A reflected signal, indicative of the downhole parameter being measured, then returns through the same optic fiber 28 to circulator 44 and onto inward propagating optic fiber 46, which directs the light signal through optical receiver 48 and to instrumentation unit 16 for acquisition, storage, and interfacing.

In this prior art approach, it should be noted that when the signal is initially sent to the sensor assembly 34, the aforementioned backscattering effects present in optic fiber 28 are sent to the optical receiver 48, and generate noise that can perturb the reflected signal coming from the sensor assembly 34. The longer the optical pathway distance 'd' from the instrumentation unit 16 to the sensor assembly, the worse this problem will be.

Figure 2:
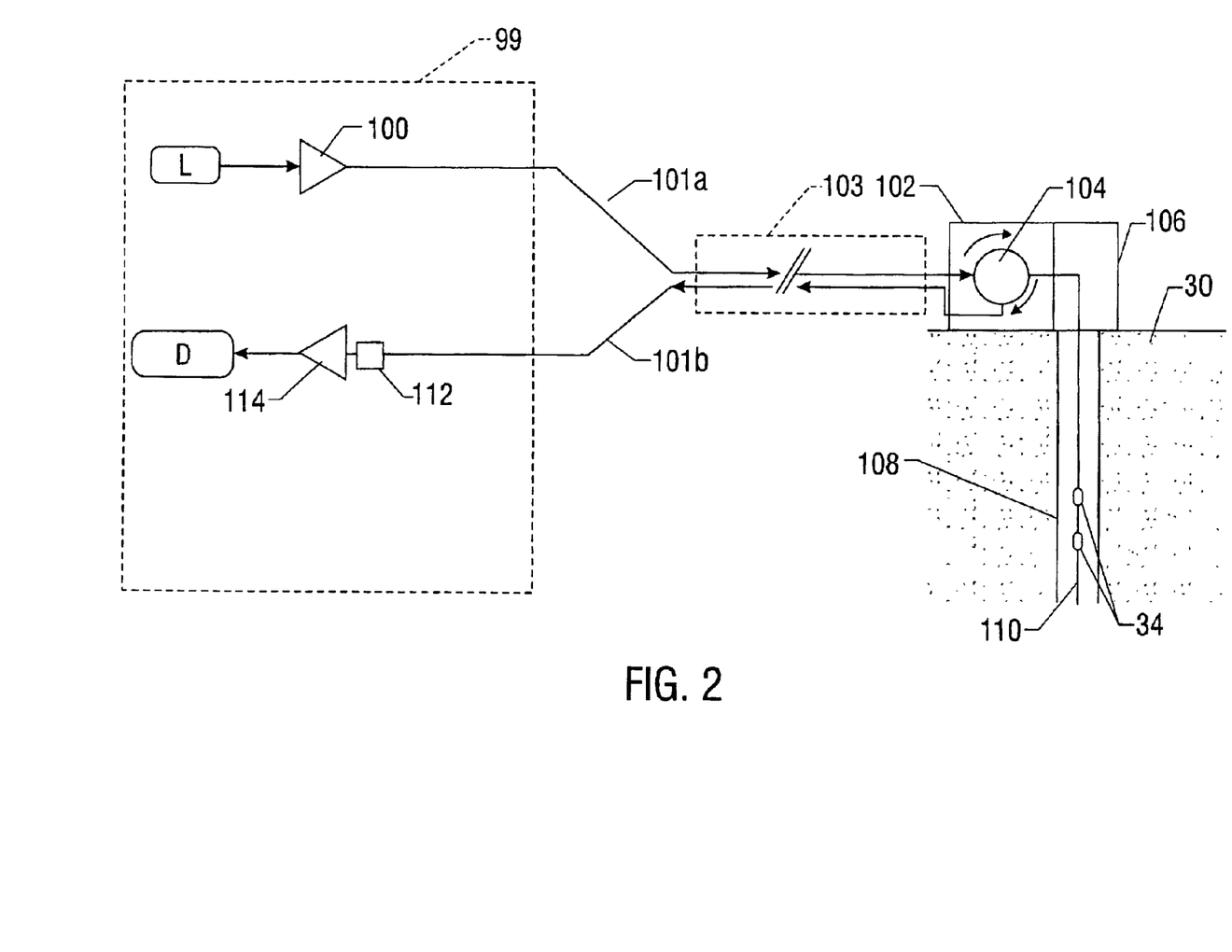
FIG. 2 illustrates a remote deployment of the fiber optic circulator having dedicated forward and return lines in a downhole environment according to the system of the present invention.

FIG. 2 illustrates a preferred embodiment of the present invention, illustrating a control system with a remotely located optical circulator 104 placed within a circulator housing 102 attached or near to wellhead assembly 106. Light source L, housed within control station 99, directs light through optical transmitter 100 to forward transmitting fiber optic cable 101a. The fiber optic cable 101a can be directly connected to wellhead assembly 106 through the optical circulator 104, or more preferably can be optically coupled to a dual-fiber-optic-cable umbilical 103 running between the surface instrumentation 99 and the wellhead assembly 106.

The fiber optic cable 101a (or umbilical 103 if used) is attached to an optical circulator 104 contained within a circulator housing 102 that is near to, or more preferably attached to or within wellhead assembly 106. The light signal travels through the optical circulator 104 and out through fiber optic downhole cable 110 that is coupled to the optical circulator 104 and which extends down into well bore 108 drilled into subterranean earth 30. As is well known, downhole cable 110 can be attached to various structures in well bore 108 (e.g., a production tube or casing; not shown) to measure various downhole parameters (e.g., pressure, temperature, flow rate, resistivity, capacitance, magnetism, etc.). The light signal travels through the downhole cable 110 to a fiber optic sensor or sensor assemblies 34, and the reflected signal indicative of the measured parameter(s) proceeds back up to optical circulator 104. The reflected signal is then directed out through a port of the circulator to a second and separate return optic fiber cable 101b in the umbilical 103. Either way, the reflected light signal is eventually passed to control station 99 by return optic fiber cable 101b, and specifically through a photo-intensity detector 112 to an optical receiver/detector 114 coupled to a display/data storage means D such as an oscilloscope, monitor, or computer.

As one will appreciate from FIG. 2, the forward transmitting fiber optic cable 101a which sends the signal to the sensor assemblies 34 is decoupled from the return optic fiber cable 101b by the circulator 104 within the circulator housing 102 positioned at or near wellhead assembly 106. In other words, the backscattering and other noise-creating phenomenon mentioned earlier will have minimal or no effect on the reflected signal from the sensors because such noise signals emanating from fiber optic cable 101a will never impinge upon the optical receiver 114 in the control station 99. Thus, the use of the remotely deployed optical circulator 104 in conjunction with a second return optic fiber cable 101b significantly lowers the optical noise in the optical signal-to-noise ratio and optical backscatter, allowing for a significant extension of the distance over which fiber optic monitoring for both transoceanic and terrestrial applications can be applied. Moreover, the disclosed configuration allays concerns regarding the types of couplers and connectors that can be used and which might otherwise create or negatively react to noise. As a result, higher loss, higher noise coupler and connectors (e.g. physical angle, ball lens, grin-rod lens, etc.) can be used to couple components such as sensors together in the disclosed configuration without suffering from the backscatter noise that such couplers or connectors provide.

As described above, and in accordance with the present invention, optical circulator 104 can be at or near the remotely located wellhead assembly, meaning that the optical circulator can be "at" the wellhead assembly in an isolated housing assembly that is attached to or within the wellhead assembly, or in an isolated housing in near proximity to the wellhead assembly. Optionally and equally acceptable, the optical circulator can be remotely located on a platform a short distance removed from the wellhead assembly, and can be connected by a short umbilical to the wellhead assembly.

FIG. 2 depicts the embodiment of optical circulator 104 being contained within circulator housing 102 attached to wellhead assembly 106. In this embodiment, forward transmitting fiber optic cable 101a enters circulator housing 102 through any well known pressure-tight, water-tight feed-through gland in the outer wall of the housing (not shown) and into the optical circulator 104. Return optic fiber cable 101b passes out of optical circulator 104 through a similar (or even the same) pressure-tight, water-tight feed-through gland in the outer wall of the housing (not shown) in its return to control station 99. Fiber optic downhole cable 110 passes from optical circulator 104 through a second and separate pressure-tight feed-through gland into wellhead assembly 106, and downhole to the sensor assembly 34.

Circulator housing 102 is preferably a low (ambient) pressure and temperature chamber having walls that are water and pressure tight, and are impervious to broad temperature changes. The interior of the circulator housing 102 where the circulator 104 is positioned can be dry, an evacuated vacuum, or can be filled with an appropriate fluid (e.g. oil) or gas (e.g. nitrogen). Typically, a gasket, forming a metal-to-metal environmental seal is provided between the circulator housing 102 and the wellhead assembly 106.

As is well known, the light source L can be a device such as a semiconductor laser, a broadband light source such as a laser diode, or any other source of coherent light. Most preferably, the light source L is a laser such as a Zeeman laser, Nd:YAG laser, Nd:glass ring laser, femtosecond Ti:sapphire laser, or any other acceptable laser light source known in the art. The light produced by light source L can have a wavelength of, for example, 1.5 $\mu$m, or may be tunable to varying wavelengths in a manner appropriate for interrogating the sensor assemblies 34 being used downhole. Depending on the application and the nature of the sensors in the sensor assemblies 34, Light source L can be a pulsed light signal whose time decay constant is to be assessed, a periodic pulsed signal, a particular wavelength tuned to interact with fiber Bragg gratings, or any other source suitable for stimulating the sensors.

Optic fibers 101a and 101b, the fiber in umbilical 103, and/or the downhole fiber 110 are of the type known in the art, and are preferably standard 125-micron diameter communication cables. The fiber may be made of any glass, silica, phosphate glass, glass and plastic, plastic, or other materials used for making optical fibers and may optionally include any appropriate dopants as required, although glass cables are preferred for high temperature downhole applications. Other optical waveguides could be used as well, such as multi-mode, birefringent, polarization maintaining, polarizing, multi-core, or multi-cladding, or flat or planar waveguides. As used herein, the term "optic fiber" includes the above-described fibers and waveguides.

As noted earlier, although the fiber optic cables between the control station 99 and the wellhead assembly 106 are capable of being deployed individually, they are preferably constitute an umbilical 103 or similar fiber bundle. Attachment to the umbilical 103 can be by any optical coupling method known in the art. When the system of the invention is deployed in a harsh environment, such as downhole within an oil well, the downhole fiber 110, fiber bundle 101a/101b, or umbilical 103 can be deployed inside the casing or embedded in the cement outside of the casing. Alternatively, various fiber packaging and fiber production arrangements can be used, such as deploying the optic fiber(s) within a hermetically sealed capillary tube, such as the arrangement described in U.S. Pat. No. 6,016,702, the disclosure of which is incorporated herein by reference in its entirety.

The wellhead assembly 106 provides for both the feed-through and exiting of the fiber optic cables 101a/101b from the well in a safe and reliable manner, as well as a housing for optical circulator 104 within circulator housing 102. The wellhead assembly 106 can constitute any known standard wellhead known in the art, and contains a minimum of two sealing barriers to prevent leaks and is rated to the pressures, temperatures, and environmental conditions in which it will be working. In a multi-well installation, a multi-core surface cable can be run from the control station 99 to a junction box (not shown) proximate to the control station 99. The junction box can be at the surface or remotely located on the seabed proximate to the workstation, with separate optical cables running from the junction box to multiple optical circulators housed within or near the wellhead.

The optical circulator 104 employed in the present invention can be any optical circulator known in the art. Specifically, the present invention can use a multi-mode circulator, a three-port optical circulator, a four-port optical circulator, an inline optical circulator, a birefringent crystal optic circulator, a low polarization optical circulator, or a polarization-independent optical circulator, such as those described in U.S. Pat. No. 6,310,989; U.S. Pat. No. 6,377,720; U.S. Pat. No. 6,370,287; U.S. Pat. No. 6,111,695; S. K. Liaw et al., "Repeated Bidirectional Transmission Using Two 4-Port Optical Circulators and a Bidirectional EDFA without Isolators," Optical Fiber Technology, Vol. 5, pp. 253–259 (1999); and Y. Fujii, "Polarization-Independent Optical Circulator Having High Isolation Over A Wide Wavelength Range," IEEE Photonics Technology Letters, Vol. 4, pp. 154–156 (1992), all of which are incorporated herein by reference in their entireties. Multiple optical circulators can also be used simultaneously, such as in the instance where multiple sites are being monitored at the same time.

Figure 3:
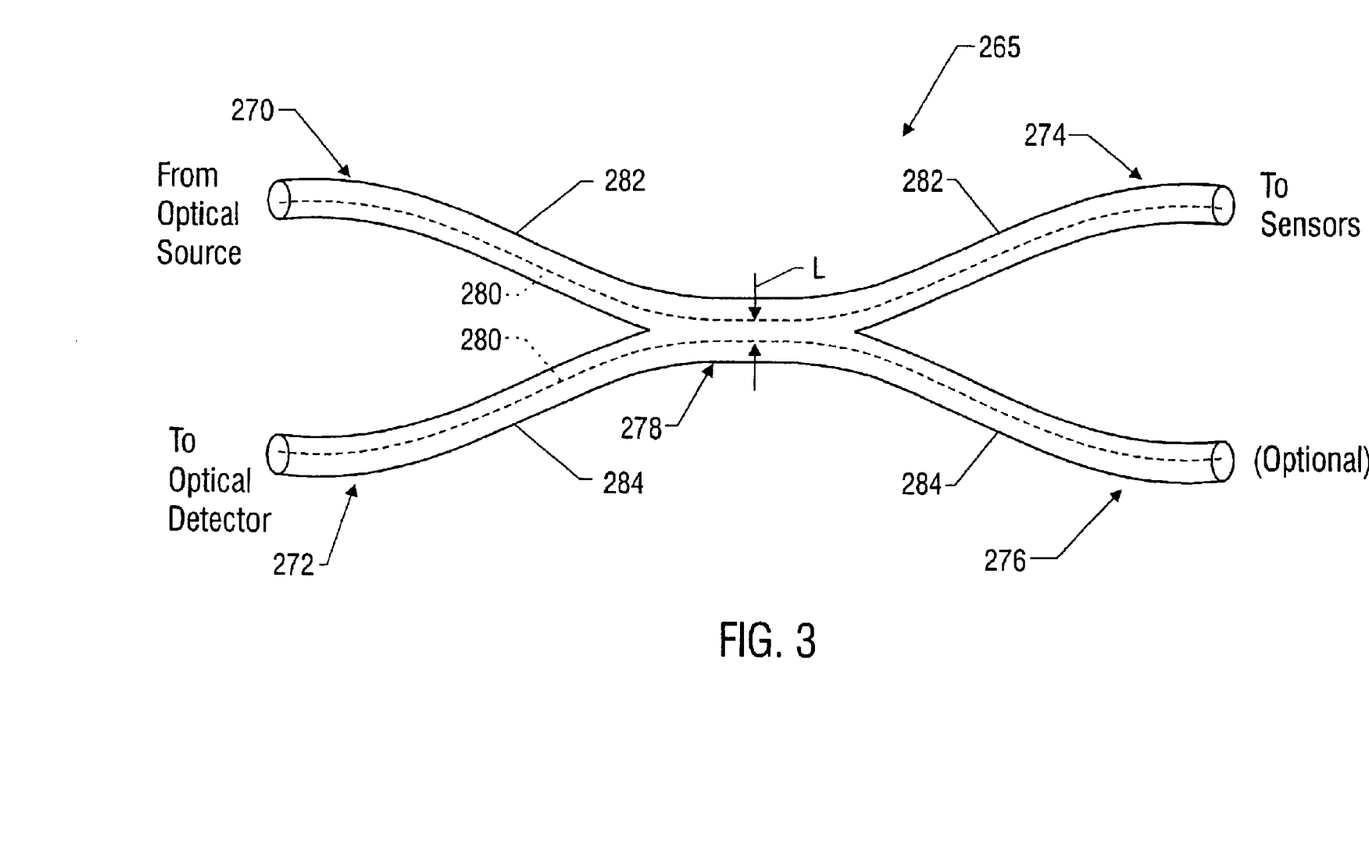
FIG. 3 illustrates an optical coupler, specifically a splitter/combiner, useful in lieu of the disclosed circulator.

Also suitable for use with the present invention in lieu of an optical circulator are other optical devices or configurations of such devices that function in the same manner as optical circulators, such as well-known fiber optic splitter/combiners. An example of a splitter/combiner 265 is shown in FIG. 3. Splitter/combiner 265 as depicted comprises a 2×2 splitter/combiner, as it has 2 pairs (270/272 and 274/276) of input/outputs. As is well known, splitter/combiner 265 is formed by fusing two pieces of fiber optic cable 282, 284 or other waveguides together so that the two cores 280 are brought into close proximity, e.g., by length L. Length L typically comprises about four wavelengths of the light that is to be transmitted within the cores 280 of the fiber optic cable. In this way, the evanescent optical field transmitting through one cable will split so that half of the light energy will continue transmitting through the original cable, and half of the light energy will transmit through the adjacent cable. Thus, in a configuration useful in the context of the disclosed invention, light from the optical source can be transmitted through cable 270 and to the sensors to be interrogated through cable 274. The reflected light from the sensors will then travel back to the splitter/combiner 265, where again half of the light will be transmitted through cable 272 and to the optical detector. (In this regard, only a 2×1 optical splitter/combiner is needed in a useful embodiment of the present invention, and thus cable 276 may be un-utilized or cut away. Optionally, cable 276 could also be coupled to other sensors, although care may need to be taken to ensure that the sensor reflections from cable 274 will not interfere from those coming from cable 276. Such interference can be allayed by using fiber Bragg gratings with different reflection wavelengths or by using cable lengths that ensure that reflections will not appear at the splitter/combiner at the same time). Thus, in an embodiment using an optical splitter/combiner 265, the detected light reflected from the sensors will experience an approximately 6 dB (25%) loss of signal strength at the detector. (An optical circulator by contrast will typically only experience an approximately 1 dB loss, and therefore may be of more utility in applications where a loss of signal strength would be less acceptable.)

The splitter/coupler 265 functions in much the same way as the disclosed optical circulator in that light reflected from the sensor is sent to the detector along a dedicated path (e.g., cable 272), making backscattering phenomenon along the forward line (e.g., cable 270) irrelevant. Therefore, the splitter/coupler 265 may, like the optical circulator, be remotely deployed from the optical source with substantial benefit. As used in this specification and in the appended claims, "circulators" should be understood to encompass devices such as splitter/combiners or other couplers ("nodes") that are capable of functioning similarly to the circulators and/or splitter/combiners disclosed herein.

Figure 4:
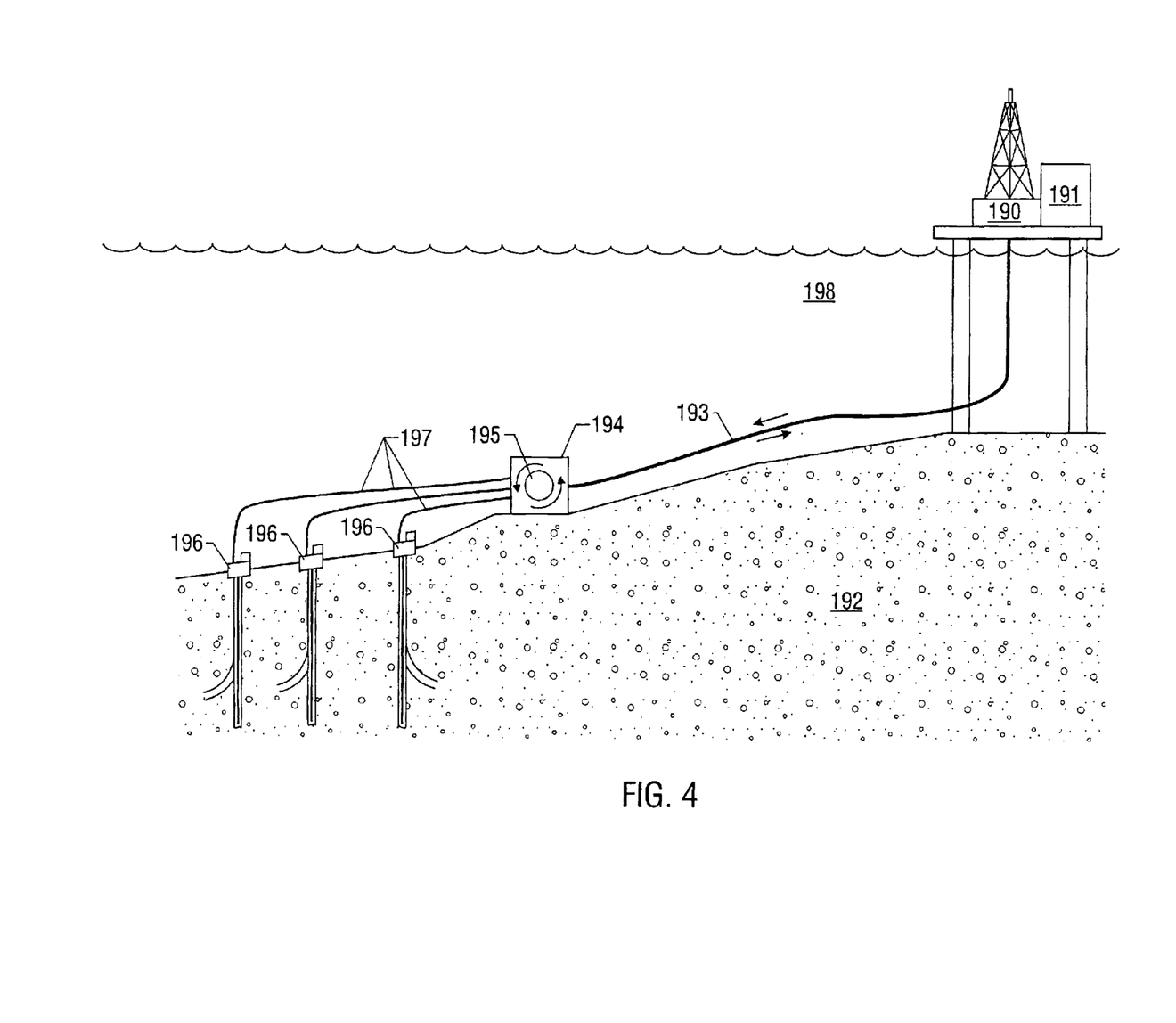
FIG. 4 illustrates the use of the system of FIG. 2 in the context of monitoring multiple remote subsea wells.

FIG. 4 shows how the embodiments of the present invention can be used in the oil and gas field to monitor deployed sensors into subsea oil and/or gas wells. While the example is given for wells 196 at the surface of the ocean floor 192, it will be appreciated that the groups of wells 196 are analogous to groups of wells positioned together on the earth's surface. The present invention is therefore well suited for control of land-based wells in addition to subsea wells.

As illustrated, optical fiber umbilical 193 runs between the instrumentation unit 191 and the wellhead assembly 194 which houses optical circulator 195 as described previously. This optical circulator 195 may be associated with a plurality of wells 196 through a multiplicity of optical fibers 197. Consequently, the optical circulator 195 can have a mulitplexer/demultiplexer (such as a wavelength dispersion multiplexer (WDM)) attached to it at the output. In this manner, the multiplicity of optical fibers 197 carry their optical signals to and from the optical circulator 195 to a plurality of wells 196 through an attached WDM.

Alternatively, the wellhead of each of the wells 196 may contain its own optical circulator, one associated with each well. Although only one platform 190 is shown, it will be appreciated that any number of platforms can be used with the disclosed system. As explained earlier, umbilical 193 would preferably contain at least separate transmission and reception cable pairs for each well to be monitored. Alternatively, in some applications, the sensors within wells 196 (not shown) could be serially connected (multiplexed) by reconfiguring optical cables 197 as is well known, although the reflectivities or number of the sensors might need to be adjusted so that a suitable amount of optical power can be sent to and received from each of the sensors within the wells. As before, because the circulator(s) 195 is/are remotely located and are connected to dedicated forward and return lines, backscatter in the cable/umbilical 193 becomes irrelevant and therefore may be made quite long. For example, the distance between the subsea wellhead assembly 194 housing the optical circulator 195 and the instrument unit 191 on the platform 190 can be about 10 km to about 60 km and could be extended to greater than 100 km in the foreseeable future.

The disclosed inventive concepts could have applicability in other contexts requiring the use of remote monitoring. For example, the disclosed system could be used, for example, in mine shafts to detect the presence of noxious and/or deadly gases (e.g. methane, acetylene), in chemical storehouses to detect dangerous conditions, in seismic monitoring situations, and to measure leaks in salt domes. These are illustrated in FIGS. 5–8, primarily for the purposes of depicting a variety of specific contexts in which a variety of parameters such as stresses, strains, pressures, temperatures, and the like, can be remotely monitored using fiber optic technology from a great distance. In each case, the present invention provides a fiber-optic-based sensor that is remotely deployed, and an optical circulator that is similarly remotely deployed in order to increase the distance over which the monitoring can occur without backscattering problems.

Figure 5:
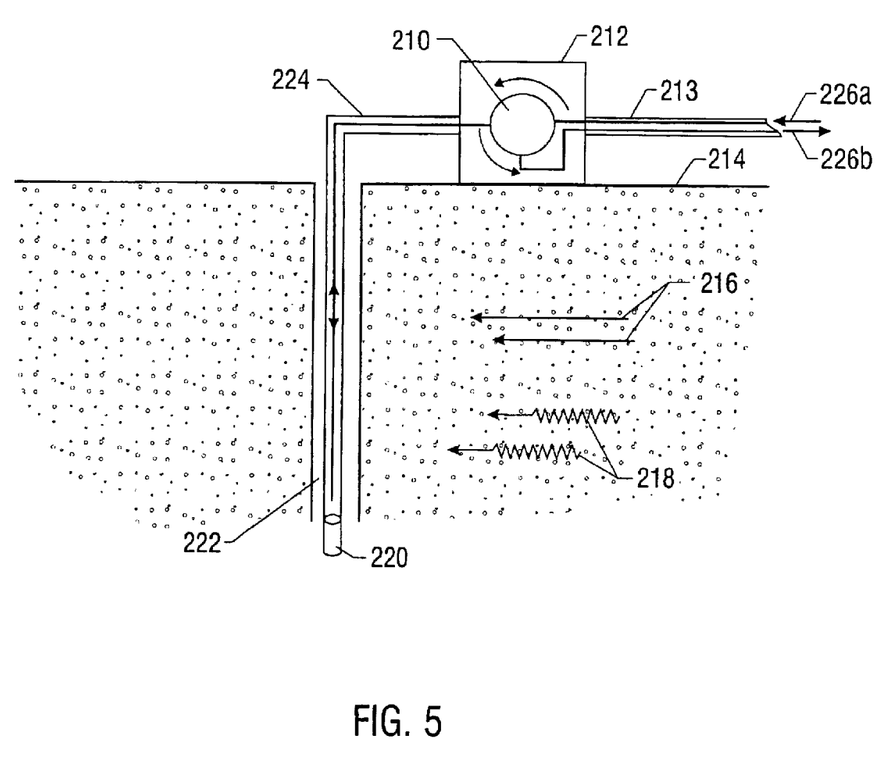
FIG. 5 illustrates the use of the present invention to monitor earth movements and other subterranean conditions with respect to a borehole.

More particularly, with reference to FIG. 5, a fiber optic cable 224 connected to at least one sensor 220 is coupled to a remotely deployed optical circulator 210 within housing 212. In this example, the system is used in conjunction with a land-based well, and hence the circulator is not coupled to a sea floor-based well head. The cable/sensor system can be suspended vertically into a borehole 222 or other monitoring type hole formed into the earth 214. This fiber optic cable 224 can be coupled to other sensor monitoring cables present in the hole, or can be a stand-alone fiber optic cable.

Of course, many such cables 224 can be employed, and each cable 224 might contain, or be coupled to, multiple sensors 220, although only one cable and sensor are shown. Typically, cable 224 is lowered into the borehole 222 using a weight placed at its lower end. The fiber optic cable 224 and/or associated sensor(s) 220 are susceptible to pressure-induced bending, which can be used to determine the condition of the earth 214 surrounding the borehole 222. Such bending could be caused by any number of seismic events, for example, by lateral spreading or shifting of the earth 214, as depicted by arrows 216, as might occur due to tectonic plate shifting near a fault line, by an earthquake as depicted by arrows 218, or by an intentionally-created disturbance as might be used in seismology. When such a stress is detected, reflected light travels from cable 224 through the optical circulator 210 and onto dedicated return optic fiber cable 226b, unaffected by optical backscatter present on forward transmitting fiber optic cable 226a. As noted previously, optic fiber cables 226a and 226b can be very long, allowing for extremely remote monitoring over many kilometers.

Figure 6:
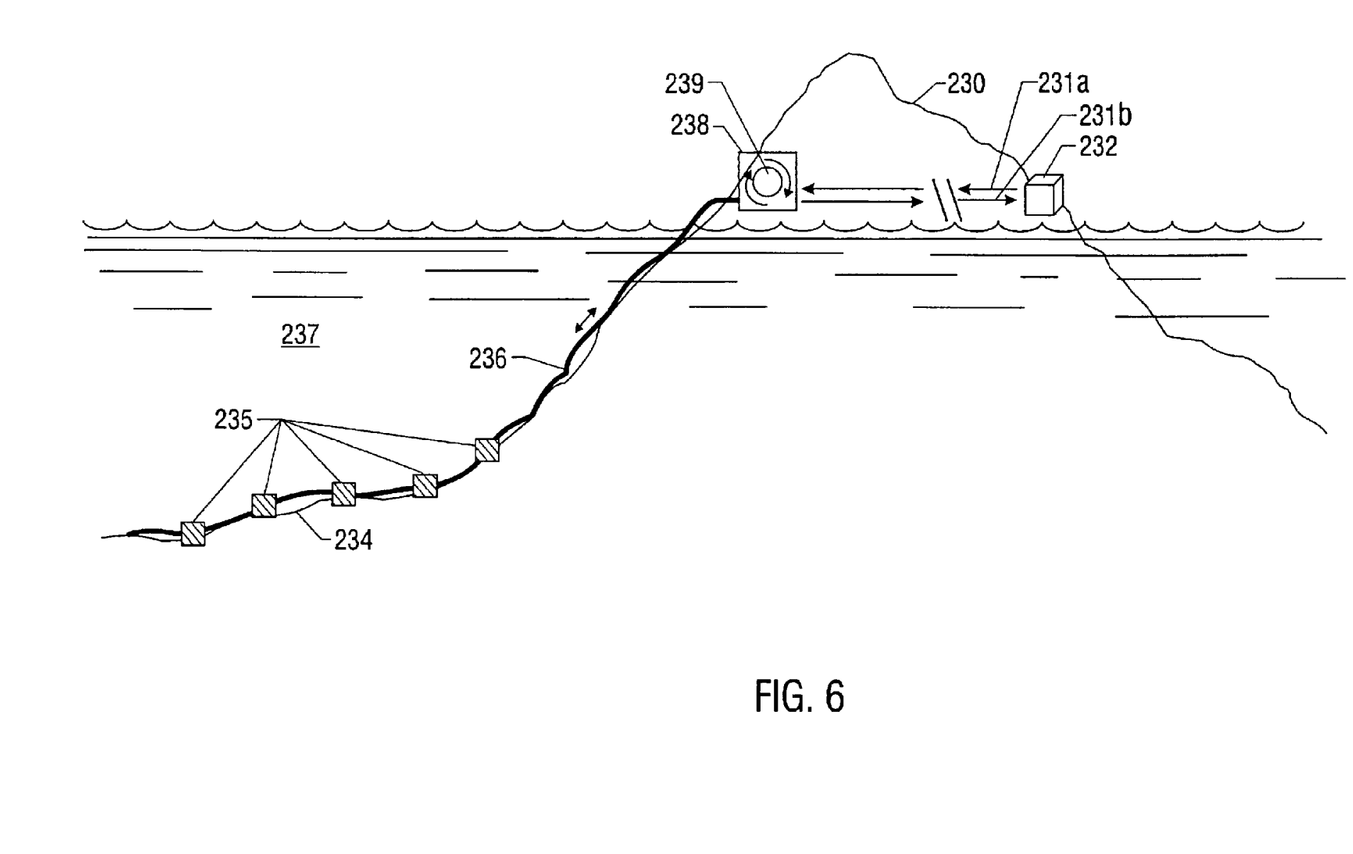
FIG. 6 illustrates the use of the present invention to monitor pressure changes along the ocean floor.

FIG. 6 illustrates a fiber optic cable 236 containing imbedded pressure sensors 235 which are used to monitor water pressure at various depths. Such an application could also be useful in seismic exploration, whether on land or at sea, with the sensors 235 being remote sensor arrays including hydrophones, geophones, or a combination of both, such as those described in U.S. Pat. No. 6,256,588, which is incorporated herein by reference in its entirety. One end of the fiber optic cable 236 is coupled to an optical circulator 239 within housing 238, which in turn is connected to a monitoring station 232 at a remote location by an umbilical (not shown) that preferably contains a dedicated transmission fiber optic cable 231a and a dedicated return fiber optic cable 231b. As in the previous embodiments, the length of fiber optic cables 231a/231b (and/or the associated umbilical) can be quite long, e.g., 50 km. A laser or light source housed at the monitoring station 232 directs light down the forward transmitting fiber optic cable 231a through the optical circulator 239 and down the length of cable 236. If, as in a preferred embodiment, the sensors 235 constitute fiber Bragg gratings embedded within the core of the fiber, each grating could have a unique Bragg reflection wavelength ($\lambda_B$) which is shifted in accordance with the pressure to which it is exposed on the ocean floor 234. Such an arrangement constitutes wavelength-division multiplexing of the sensors along the fiber, although other well-known means of multiplexing the sensors can be used. As in the other embodiments, the light reflected back from sensors 235 is routed by optical circulator 239 onto a dedicated return fiber optic cable 231b within the umbilical, thus mitigating the effects of backscatter generated within the forward fiber optic cable 231a and allowing the distance between the optical circulator/housing 239/238 and the monitoring station 232 to be significant. Again, several optical cables 236 could be coupled to the optical circulator/housing 239/238, or several optical cables 236 and optical circulators 239 with umbilical systems could be coupled to one or more monitoring stations 232.

Figure 7:
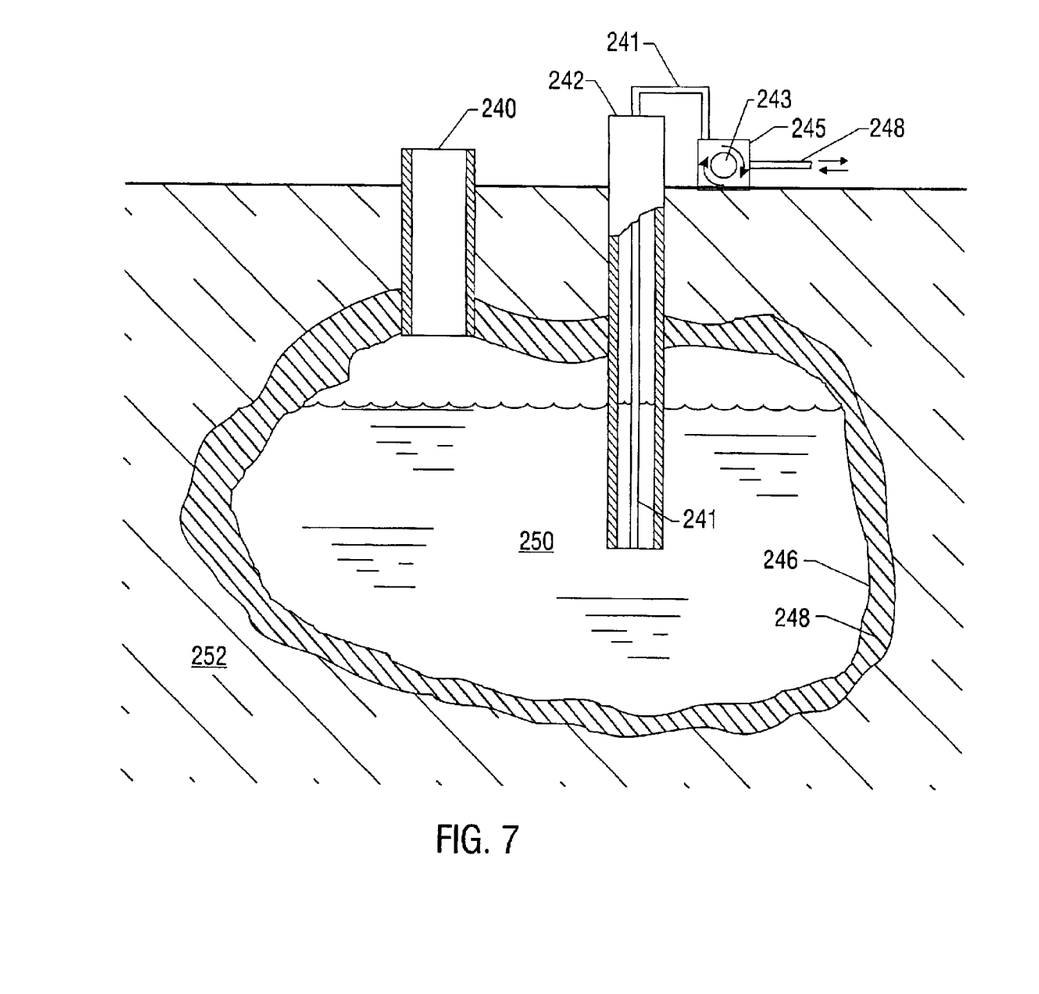
FIG. 7 illustrates the use of the present invention to monitor an underground reservoir.

FIG. 7 shows the utility of the disclosed invention in the context of a subterranean cavern or salt dome 246 having an almost impermeable rock salt (halite) barrier 248. Such a facility allows for the storage of valuable hydrocarbon inventories and/or allows waste to be permanently disposed within the earth 252. As those skilled in the art will realize, it is often necessary to monitor such caverns 246 for leakage due to safety, environmental, and economic reasons. Accordingly, a fiber optic cable 241 containing or coupled to pressure or temperature sensors such as multiplexed fiber Bragg gratings (not shown) can be deployed through inlet conduit 242 and into the reservoir 250. Outlet conduit 240 can be used for venting or other purposes. Fiber optic cable 241 is connected to the optical circulator 243 within housing 245 that is in turn coupled to umbilical 248 and a remote monitoring station (not shown) as in the other disclosed embodiments. The sensors within the fiber optic cable 241 can monitor such parameters as reservoir volume change by monitoring a change in hydrostatic pressure on the sensors (indicative of leakage), or temperature change (indicating potential for a fire). Although an underground storage reservoir is shown, the technique has equal applicability to ground-base storage devices, such as gasoline tanks.

Figure 8:
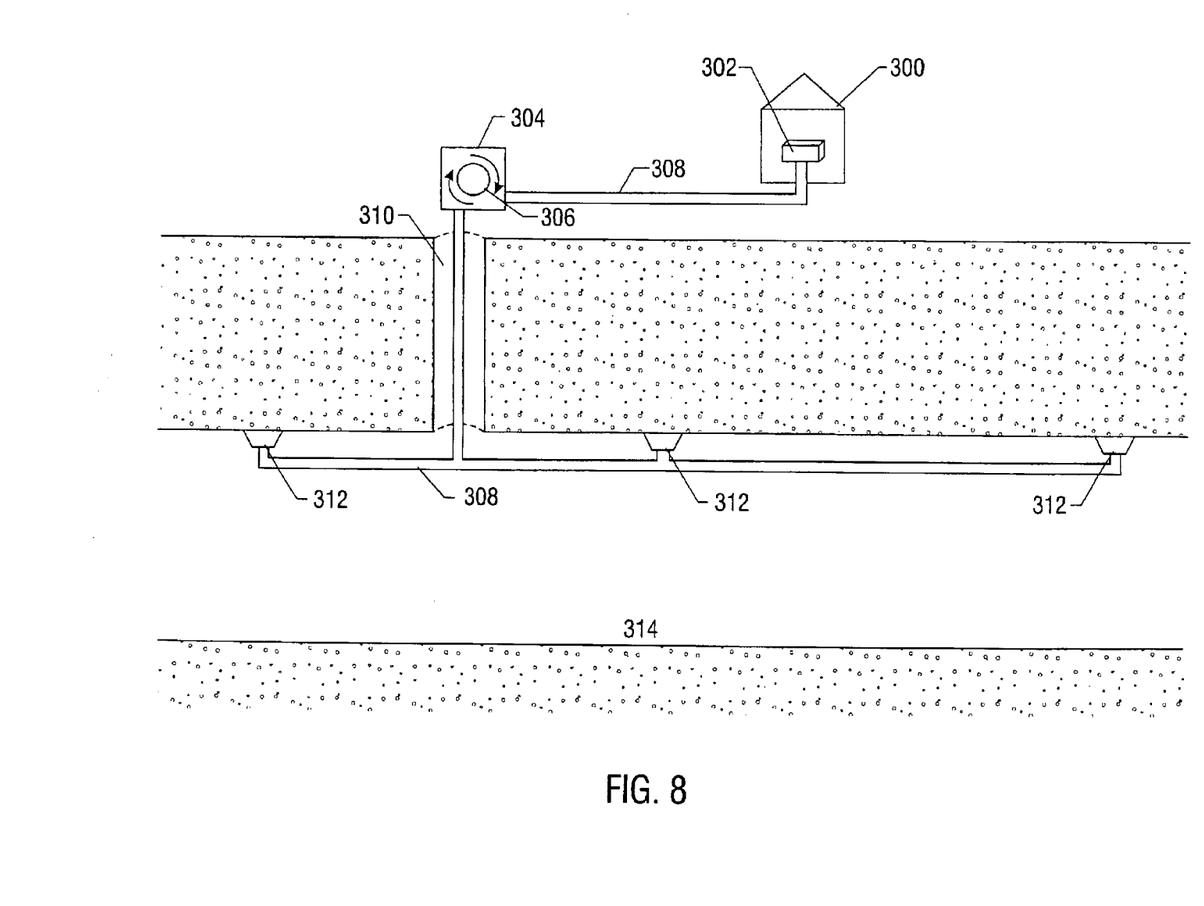
FIG. 8 illustrates the use of the present invention to monitor toxic gases within a mine.

FIG. 8 shows the utility of the disclosed invention in the context of monitoring underground mines for dangerous atmospheric conditions such as poisonous gases using a remote environmental warning system. A remote central monitoring station 300 having a control system 302 is coupled by a dual-fiber-optic umbilical 308 to a remotely deployed optical circulator 306 within housing 304 as in the other embodiments. The optical circulator 306 is coupled to sensor fiber optic cable 308 deployed through a borehole 310 that couples the surface to a mineshaft 314. Fiber optic cable 308 is in turn connected to remote sensing units (RSU) 312, optical devices whose reflection response varies when in the presence of certain chemicals. Suitable RSUs useable in the context of this disclosure are well known and contain gas sensors, optical circuitry, and the like. As with the other embodiments, the use of the remotely deployed optical circulator 306, in conjunction with the forward and return cables within umbilical 308, allows for remote sensing of harmful gases, which can be critically important when potentially lethal gases are detected within the mine shaft 314.

Although this disclosure contemplates that the remote deployment of the optical circulator from the optical source can span several miles (e.g., 1–100 miles) as is disclosed in the embodiments herein, shorter or longer distances are possible. In this regard, what constitutes "remote deployment" should be understood in context. For example, an optical circuit as might be found in an optics laboratory which has a circulator placed only a few feet away from the optical source should not be understood to be remotely deployed as used in this disclosure, particularly if there is no technical reason or desire that the source and the circulator be displaced from one another in the application. By contrast, some applications (e.g., room to room monitoring) might constitute an technically intentioned and reasoned desire to separate the source from the circulator, and in this sense the circulator can be said to be remotely deployed even if the separation between the components comprises only, for example, tens of feet. In other words, remote deployment should be understood as constituting the intentional separation of the source and the circulator for a technical reason, such as, for example, the reduction of backscattering phenomenon as is disclosed herein.

"Coupled" as used herein should not be understood to require direct contact between the components that are coupled, but rather should be understood in a relational or communicative sense that recognizes the possibility of intermediary components. Thus, and for example, a sensor can be said to be coupled to the circulator even if some intermediary component, such as an length of cable, a coupler or connector, or polarizer, etc., intervenes between the two.

The remotely deployed optical sensing system disclosed herein has been described in terms of preferred embodiments. However, it will be apparent that a wide variety of configurations and applications are possible that remain within the scope of the present invention, as defined by the following claims and their equivalents.

What is claimed is:

1. A system for monitoring at least one parameter, comprising:
   an optical source coupled to at least one forward optical waveguide for transmitting incident light onto the forward optical waveguide;
   an optical detector coupled to at least one return optical waveguide for receiving reflected light from the return optical waveguide;
   at least one optical circulator remotely deployed from at least the optical source, wherein the forward optical waveguide and the return optical waveguide are coupled to the circulator; and
   at least one fiber-optic based sensor coupled to the circulator and responsive to the parameter, wherein the sensor is deployed down a borehole within the earth, is interrogated by the incident light, and produces the reflected light.

2. The system of claim 1, wherein the circulator is also remotely deployed from the optical detector.

3. The system of claim 1, wherein the source and the detector are proximate to each other.

4. The system of claim 1, wherein the source and the detector are integrated within a component.

5. The system of claim 1, wherein the forward and return waveguides are integrated within a cable.

6. The system of claim 1, wherein the sensor comprises at least one Bragg grating.

7. The system of claim 1, wherein the at least one fiber-optic based sensor comprises a plurality of sensors which are not multiplexed and which are each coupled to the circulator.

8. The system of claim 1, wherein the at least one circulator comprises a plurality of circulators, wherein each circulator is coupled to a forward and return optical waveguide, and wherein at least one sensor is coupled to each circulator.

9. The system of claim 1, further comprising a mine, and wherein the sensor comprises a toxic gas sensor, and wherein the sensor is deployed within the mine.

10. The system of claim 1, wherein the sensor detects a seismic event.

11. The system of claim 1, wherein the circulator comprises a splitter/combiner.

12. The system of claim 1, wherein the circulator is housed in a well head.

13. The system of claim 12, wherein the well head is positioned on a sea bed.

14. The system of claim 1, wherein the borehole comprises an oil/gas well.

15. The system of claim 14, further comprising a production pipe deployed within the oil/gas well, and wherein the sensor is coupled to the production pipe.

16. The system of claim 1, further comprising a reservoir, wherein the sensor is deployed within the reservoir to monitor a change in the reservoir.

17. The system of claim 16, wherein the reservoir comprises a tank, and wherein the change comprises leakage from the tank.

18. The system of claim 16, wherein the reservoir comprises an underground storage reservoir, and wherein the change comprises leakage from the reservoir.

19. A system for monitoring at least one parameter, comprising:
   an optical source coupled to at least one forward optical waveguide for transmitting incident light onto the forward optical waveguide;
   an optical detector coupled to at least one return optical waveguide for receiving reflected light from the return optical waveguide;
   at least one optical circulator remotely deployed from at least the optical source, wherein the forward optical waveguide and the return optical waveguide are coupled to the circulator; and
   at least one fiber-optic based sensor coupled to the circulator and responsive to the parameter, wherein the at least one fiber-optic based sensor comprises a plurality of sensors multiplexed on a single optical waveguide that are interrogated by the incident light and produce the reflected light.

20. The system of claim 19, wherein the at least one sensor is deployed on the seabed to measure at least one hydrostatic pressure.

21. A method for monitoring at least one parameter, comprising:
   deploying at least one sensor down a borehole in the earth;
   transmitting an incident light from a optical source onto at least one first optical waveguide;
   receiving the incident light from the first optical waveguide at least one node remotely deployed from the optical source;
   transmitting the incident light from the node to the least one sensor;
   receiving reflected light from the sensor at the node; and
   transmitting the reflected light from the node to an optical detector through a second optical waveguide different from the first optical waveguide.

22. The method of claim 21, wherein the node is also remotely deployed from the optical detector.

23. The method of claim 21, wherein the source and the detector are proximate to each other.

24. The method of claim 21, wherein the source and the detector are integrated within a component.

25. The method of claim 21, wherein the first and second waveguides are integrated within a cable.

26. The method of claim 21, wherein the at least one sensor comprises a plurality of sensors multiplexed on a single optical waveguide.

27. The method of claim 21, wherein the at least one sensor comprises a plurality of sensors which are not multiplexed and which are each coupled to the node.

28. The method of claim 21, wherein the at least one node comprises a plurality of nodes, wherein each node is coupled to a first and second optical waveguide, and wherein at least one sensor is coupled to each node.

29. The method of claim 21, further comprising deploying the sensor within a mine, and wherein the reflected light is indicative of the presence of toxic gas within the mine.

30. The method of claim 21, wherein the reflected light is indicative of a seismic event.

31. The method of claim 21, wherein the node comprises an optical circulator.

32. The method of claim 21, wherein the node comprises a splitter/combiner.

33. The method of claim 21, wherein the node is housed in a well head.

34. The method of claim 33, wherein the well head is positioned on a sea bed.

35. The method of claim 21, wherein the borehole comprises an oil/gas well.

36. The method of claim 35, further comprising deploying a production pipe within the oil/gas well, and wherein the sensor is coupled to the production pipe.

37. The method of claim 21, further comprising deploying the sensor within a reservoir, wherein the reflected light is indicative of a change within the reservoir.

38. The method of claim 37, wherein the reservoir comprises a tank, and wherein the change comprises leakage from the tank.

39. The method of claim 37, wherein the reservoir comprises an underground storage reservoir, and wherein the change comprises leakage from the reservoir.

40. A method for monitoring at least one parameter, comprising:
    transmitting an incident light from a optical source onto at least one first optical waveguide;
    receiving the incident light from the first optical waveguide at least one node remotely deployed from the optical source;
    transmitting the incident light from the node to at least one sensor, wherein the sensor comprises at least one Bragg grating;
    receiving reflected light from the sensor at the node; and
    transmitting the reflected light from the node to an optical detector through a second optical waveguide different from the first optical waveguide.

41. The method of claim 40, further comprising deploying the at least one sensor on the sea bed, and wherein the reflected light is indicative of hydrostatic pressure.

* * * * *

UNITED STATES PATENT AND TRADEMARK OFFICE
CERTIFICATE OF CORRECTION

| | | |
|---|---|---|
| PATENT NO. | : 6,933,491 B2 | Page 1 of 1 |
| APPLICATION NO. | : 10/317703 | |
| DATED | : August 23, 2005 | |
| INVENTOR(S) | : Maida, Jr. | |

It is certified that error appears in the above-identified patent and that said Letters Patent is hereby corrected as shown below:

Column 12, Claim 21, Line 30: After "waveguide" and before "at", insert --at--

Column 12, Claim 21, Line 32: Before "least", insert --at--

Signed and Sealed this

Sixteenth Day of January, 2007

JON W. DUDAS
*Director of the United States Patent and Trademark Office*